US006556001B1

(12) United States Patent
Wiegand et al.

(10) Patent No.: US 6,556,001 B1
(45) Date of Patent: Apr. 29, 2003

(54) HIGHLY TIME RESOLVED IMPEDANCE SPECTROSCOPY

(76) Inventors: Gerald Wiegand, 25200 Carlos Bee Blvd., Apt. 382, Hayward, CA (US) 94542; Erich Sackman, Am Hochacker 47, D-81827 Munich (DE)

( * ) Notice: Subject to any disclaimer, the term of this patent is extended or adjusted under 35 U.S.C. 154(b) by 0 days.

(21) Appl. No.: 09/675,705

(22) Filed: Sep. 29, 2000

(51) Int. Cl.$^7$ ................................................. G01N 3/32
(52) U.S. Cl. .................. 324/76.21; 324/71.1; 324/71.2; 73/808
(58) Field of Search .............................. 324/76.21, 718, 324/551, 71.1, 76.22, 71.2; 73/808, 866; 204/196.06, 196.36, 404

(56) References Cited

U.S. PATENT DOCUMENTS

| | | | | |
|---|---|---|---|---|
| 4,099,117 A | * | 7/1978 | Erath ........................... | 324/357 |
| 4,658,365 A | * | 4/1987 | Syrett et al. ................. | 205/724 |
| 4,894,376 A | * | 1/1990 | Morad et al. ........... | 514/255.06 |
| 5,006,786 A | * | 4/1991 | McKubre et al. ........... | 204/404 |
| 5,797,840 A | * | 8/1998 | Akselrod et al. ........... | 600/300 |
| 5,807,272 A | | 9/1998 | Kun et al. ................... | 600/547 |
| 6,151,969 A | * | 11/2000 | Miller et al. ................ | 324/71.1 |

OTHER PUBLICATIONS

Nunes, et al., "On the application of the Wigner–Ville distribution to broadband reflectometry," *Fusion Engineering and Design 43* :441–449(1999) No month available.
Urquidi–MacDonald, et al., "Application of Kramer–Kronig transforms in the analysis of electrochemical impedance data," *Journal of the Electrochemical Society 133*:2018–2024 (1986) No month available.
Yu and Lu, "Short–time Fourier transform and wavelet transform with Fourier–domain processing," Applied Optics 33:5262–5270 (1994) Aug. 10, 1994.
Cornell et al., A Biosensor that Uses Ion–Channel Switches. *Nature.* 387, p. 580–583 (1997) Jun.
Gabrielli, Identification of Electrochemical Processes by Frequency Response Analysis, *Technical Report No.* 004/83. (1983) Aug.
Gabrielli, Use and Applications of Electrochemical Impedance Techniques, *Technical Report No.* part. No. 12860013. (1990). Mar.
Gritsch et al., Impedance Spectroscopy of Porin and Gramicidin Pores Reconstituted into Supported Lipid Bilayers on Indium–Tin–Oxide Electrodes. *Langmuir.* 14 (11), 3118–3125 (1998). Apr.
Harris, On the Use of Windows for Harmonic Analysis with the Discrete Fourier Transform. *Proceedings of the IEEE* 66 (1), 51–83 (1978). No month available.
Liu et al., Time resolved impedance response of guillotined aluminium under galvanostatic polarization. *Acta Metallurgica Sinica*, 10 (14), 297–303 (1997). Aug.
Popkivov, Fast time–resolved impedance spectroscopy for investigation under nonstationary conditions. *Electrochimica Acta, GB, Elsevier Science Publishers, Banking*, 41 (7), 1023–1027 (1996). No month available.
Popkirov et al., A New Impedance Spectrometer for the Investigation of Electrochemical Systems. *Rev. Sci. Instrum.* 63 (11), 5366–5372 (1992). Nov.

(List continued on next page.)

Primary Examiner—N. Le
Assistant Examiner—Vincent Q. Nguyen

(57) ABSTRACT

A highly time resolved impedance spectroscopy that enhances the measurement of the dynamics of non-stationary systems with enhanced time resolution. The highly time resolved impedance spectroscopy includes an optimized, frequency rich a.c., or transient, voltage signal is used as the perturbation signal, non-stationary time to frequency transformation algorithms are used when processing the measured time signals of the voltage and current to determine impedance spectra which are localized in time; and the system-characterizing quantities are determined from the impedance spectra using equivalent circuit fitting in a time-resolution-optimized form.

35 Claims, 11 Drawing Sheets

OTHER PUBLICATIONS

Popkirov et al., Effect of sample nonlinearity on the performance of time domain electrochemical impedance spectroscopy. *Electrochimica Acta, GB, Elsevier Science Publishers, Banking*, 40 (15), 2511–2517 (1995). No month available.

Popkirov et al., Optimization of the Perturbation Signal for Electrochemical Impedance Spectroscopy in the Time Domain. *Rev. Sci. Instrum.* 64 (11), 3111–3115 (1993).

Rioul et al., Wavelet and Signal Processing in *Signal Processing Technology and Applications*. Edited by J.G. Ackenhusen (The Institute of Electrical and Electronics Engineers, Inc., New York, p. 85–109 (1995). No month available.

Steinem et al., Impedance Analysis of Ion Transport Through Gramicidin Channels Incorporated in Solid Supported Lipid Bilayers. *Bioelectrochemistry and Bioenergetics*. 42 (2), 213 (1997). No month available.

Wiegand et al., Fast Impedance Spectroscopy: General aspects and performance study for single ion channel measurements, *Review of Scientific instruments* 71(6): pp 2309–2320 (2000). Jun.

Wiegand et al, Steps towards ion–channel characterization on solid substrates, *Meeting abstract of the 43rd Annual Meeting of the Biophysical Society, in Baltimore Mayland*, Feb. 13–17, (1999).

* cited by examiner

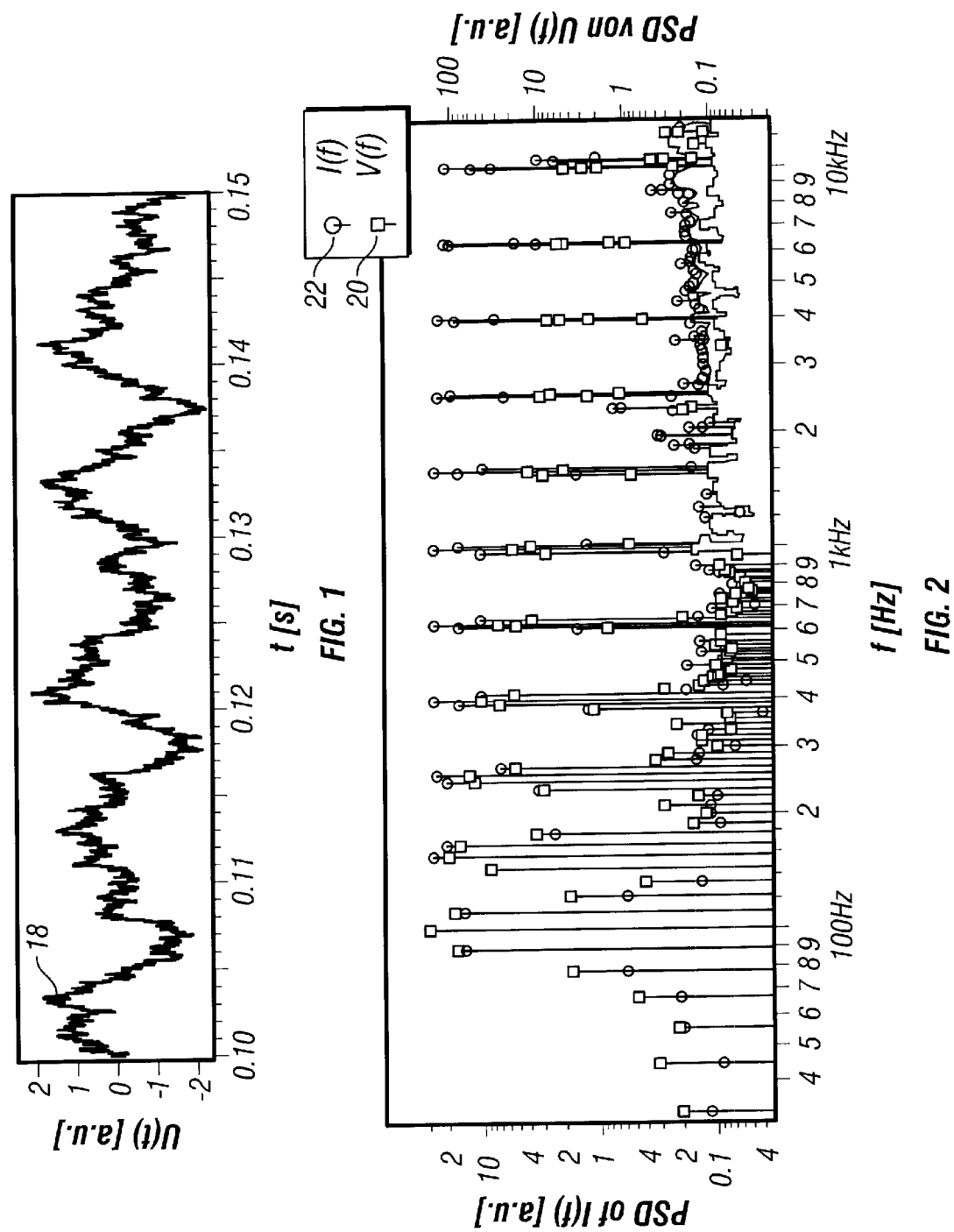

| Simulation | | Fast Model | | Gigaohm Model | |
|---|---|---|---|---|---|
| Structured Noise Signal | | | | | |
| $U_{0,tot}$ (V) | Any Number | $U_{0,tot}$ (V) | 0.05 | $U_{0,tot}$ (V) | 0.1 |
| $n$ | 6 | $n$ | 11 | $n$ | 5 |
| Contained Frequencies | | | | | |
| $F_i$ (Hz) | $U_{0,i}/U_{0,1}$ | $F_i$ (Hz) | $U_{0,i}/U_{0,1}$ | $F_i$ (Hz) | $U_{0,i}/U_{0,1}$ |
| 371.1 | 1 | 100 | 1 | 100 | 1 |
| 1113 | 0.334 | 158.5 | 0.631 | 239.9 | 0.646 |
| 1855 | 0.2 | 251.2 | 0.398 | 575.4 | 0.417 |
| 4082 | 0.091 | 398.1 | 0.251 | 1380 | 0.270 |
| 8906 | 0.417 | 631.0 | 0.158 | 3311 | 0.174 |
| 19667 | 0.019 | 1000 | 0.1 | | |
| | | 1585 | 0.063 | | |
| | | 2512 | 0.040 | | |
| | | 3981 | 0.025 | | |
| | | 6310 | 0.016 | | |
| | | 10000 | 0.01 | | |
| Data Analysis | | | | | |
| $\Delta N$ | 32 | $\Delta N$ | 50 | $\Delta N$ | 200 |
| $N_w$ | 256 | $N_w$ | 1024 | $N_w$ | 2048 |
| Window | (*) | Window | KB 3.5 | Window | KB 2.0 |

FIG. 6

HIGHLY TIME RESOLVED IMPEDANCE SPECTROSCOPY

RELATED APPLICATIONS

This Application claims priority to pending German patent application 19949107.0 entitled HIGHLY TIME RESOLVED IMPEDANCE SPECTROSCOPY filed Oct. 12, 1999, and pending German patent Application 10018745.5 entitled HIGHLY TIME RESOLVED IMPEDANCE SPECTROSCOPY filed Apr. 15, 2000 both of which are incorporated by reference in their entirety herein.

BACKGROUND

1. Field of the Invention

This invention relates generally to the measurement of electrical impedance and, more particularly, to electrochemical impedance spectroscopy.

2. Description of Related Art

Impedance spectroscopy is a procedure used to characterize the electrical and electrochemical properties of investigated systems, and their changes over time. Typically, an a.c. voltage signal is applied between a working electrode and a counter electrode. If applicable, a simultaneously applied d.c. bias voltage is monitored with a reference electrode. Both the applied a.c. voltage signal, as well as the current response of the system, are measured. The complex electrical resistance (termed the impedance $Z(\omega)$) of a system can be calculated as a function of the frequency from the quotients of the voltage and current signals in the frequency domain according to equation (1). The impedance values for a number of frequencies define the impedance spectrum.

$$Z(\omega) = \frac{\hat{U}(\omega)}{\hat{I}(\omega)}. \quad (1)$$

Various electrical properties of the system or electrochemical processes can be derived from the characteristics of the impedance spectra. Particularly for systems in which direct current cannot flow, a.c. or transient voltage signals must be used for investigations. Due to the high information content of impedance spectroscopy, it is frequently the preferred technique for measurement of impedance spectra. For example, in electrochemistry, impedance spectroscopy is a standard analysis technique for investigating e.g. corrosion processes, redox reactions, liquid and solid electrolytes, thin polymer films, membranes and batteries. Several papers have provided an introduction and overview of the technique and application of electrochemical impedance spectroscopy. See J. R. MacDonald: "Impedance Spectroscopy." (John Wiley & Sons, New York: 1987) and C. Gabrielli: *Technical Report No.* No. 004/83. 1983; C. Gabrielli: *Technical Report No. part.* No. 12860013. 1990.), both of which are incorporated by reference in their entirety herein.

Impedance spectroscopy is also used to characterize semiconductor materials See A. Bard: *Electrochemical Methods.* (Wiley & Sons, New York: 1980); and in biotechnology (See B. A. Cornell, Braach-Maksvytis, L. G. King et al.: "A Biosensor that Uses Ion-Channel Switches." *Nature.* 387, p.580–583 (1997). S. Gritsch, P. Nollert, F. Jähnig et al.: "Impedance Spectroscopy of Porin and Gramicidin Pores Reconstituted into Supported Lipid Bilayers on Indium-Tin-Oxide Electrodes." *Langmuir.* 14 (11), 3118–3125 (1998). C. Steinem, A. Janshoff and M. Siber: "Impedance Analysis of Ion Transport Through Gramicidin Channels Incorporated by reference in Solid Supported Lipid Bilayers." *Bioelectrochemistry and Bioenergetics.* 42 (2), 213 (1997). All of the above referenced publications are incorporated by reference in their entirety herein.

The use of impedance spectroscopy has increased greatly, particularly in the field of biotechnology. In most cases, the electrodes are modified by chemical or physical coupling of biofunctional molecules and aggregates (e.g. lipid/protein membranes). Impedance spectroscopy is also used to detect adsorption processes.

There are two forms of impedance spectroscopy: Measuring impedance spectra in the frequency domain, Method I; and in the time domain, Method II.

Method I (frequency domain procedure): In the first form, a sinusoidal signal at a constant frequency and amplitude is applied within a discrete period, and the complex impedance of this discrete frequency is determined. To obtain a spectrum, sequential signals at different frequencies are applied. The time resolution, defined as the length of time in which the determined spectra follow each other, is low in this form of impedance spectroscopy. The time for acquiring the data records that compose the spectrum is a multiple of the period of the lowest frequency contained in the spectrum. The precise duration also depends on the number of the frequencies in the spectrum. Following a frequency change, a transition period is allowed for the system to attain an equilibrium. The time resolution of a typical sequence of spectra is a few seconds to minutes depending on the observed frequency band.

Method II (time domain procedure): In the second form, a frequency rich a.c. voltage signal is applied such as square wave pulses, structured or white noise. By using Fourier transformation, the impedance spectrum can be determined from a single data record of the time course of the voltage and current signal. Therefore, the impedance spectrum is limited regarding the bandwidth and frequency resolution by the known limitations of Fourier transformation. The measurement time is normally at least as long as one period of the lowest frequency in the spectrum of interest. Usually a measuring period of several periods of the lowest frequency in the spectrum is required to sufficiently improve the signal to noise ratio. The maximum time resolution depends on the repetition rate at which the data records, or sets, for Fourier transformation are acquired. Because the impedance of all frequencies of the spectrum are measured simultaneously in this method, the time resolution is usually much better than that of the first method.

Method I is normally used to characterize stationary systems or systems exhibiting slow dynamics. Commercial devices (frequency response analyzers (FRA)), are available for these measurements. At present, method II is primarily used for measurements where the impedance spectra contain very low frequencies, for example, down to about $10^{-4}$ Hz, as required in corrosion studies.

The electrical properties of non-stationary systems, which means systems whose properties are not constant over time, cannot be measured in many cases with a sufficient time resolution by either Method I or Method II procedures of impedance spectroscopy. The time averaging effect of method I (summing for several periods of all the frequencies in the spectrum) and method II (over several periods of the lowest frequency contained in the spectrum) does not allow changes in the system over time, which are faster than the averaging time, to be resolved by a sequence of impedance spectra. The averaging time must be greatly reduced for impedance spectrometers to measure non-stationary systems with sufficient time resolution. A single impedance spectrum would then indicate the electrical states of the system localized in time. In addition, the individual spectra must be determined with high repetition rate to determine the time course of the system-characterizing quantities with a maximum time resolution.

An example of a non-stationary system that have not been able to be measured with conventional impedance spectroscopy includes lipid bilayer membranes with integrated, switching ion channels. The kinetics of many biological processes such as opening and closing ion channels in lipid bilayer membranes occurs on a time scale of a few milliseconds. These systems are highly relevant in the fields of biotechnology and human physiology.

Another example of a non-stationary system that has not been able to be measured with conventional impedance spectroscopy is metal and semiconductor interfaces with liquid and solid electrolytes with highly dynamic interface processes. In characterizing semiconductors and in the field of electrochemistry, conventional impedance spectroscopy cannot be used for many dynamic processes such as the in situ observation of rapid etching processes or the relaxation of electrochemical systems after voltage jumps since the necessary time resolution is impossible in the required bandwidths.

From the discussion above, it should be apparent that there is a need for a impedance spectroscopy method and apparatus that can measure non-stationary systems with high dynamics. The present invention fulfills this need.

SUMMARY OF THE INVENTION

A method and apparatus to measure impedance and impedance spectra in rapid sequence. Measurement of impedance, and impedance spectra, in rapid sequence provides repeated or continuous characterization of the electrical properties of the system under investigation. Highly time resolved impedance spectroscopy enhances the measurement of the dynamics of non-stationary systems due to its enhanced time resolution.

Three aspects of highly time resolved impedance spectroscopy are: (1) an optimized, frequency rich a.c., or transient, voltage signal is used as the perturbation signal; (2) non-stationary time to frequency transformation algorithms are used when processing the measured time signals of the voltage U(t) and current I(t) to determine a sequence of impedance spectra, where each spectrum is localized in time; and (3) the system-characterizing quantities are determined from the impedance spectra using equivalent circuit fitting in a time-resolution-optimized form.

BRIEF DESCRIPTION OF THE DRAWINGS

FIG. 1 is a plot versus time of an example of a structured noise voltage signal U(t).

FIG. 2 is a power spectrum density plot of structured noise voltage and current signals U(f) and I(f).

FIG. 6 is a table that shows examples of parameters for the structured noise signal and data processing for the described simulations in the "Simulations" column, and for the described measurements in the "fast model" and "Gigaohm model" columns.

DETAILED DESCRIPTION

Figure 3A:
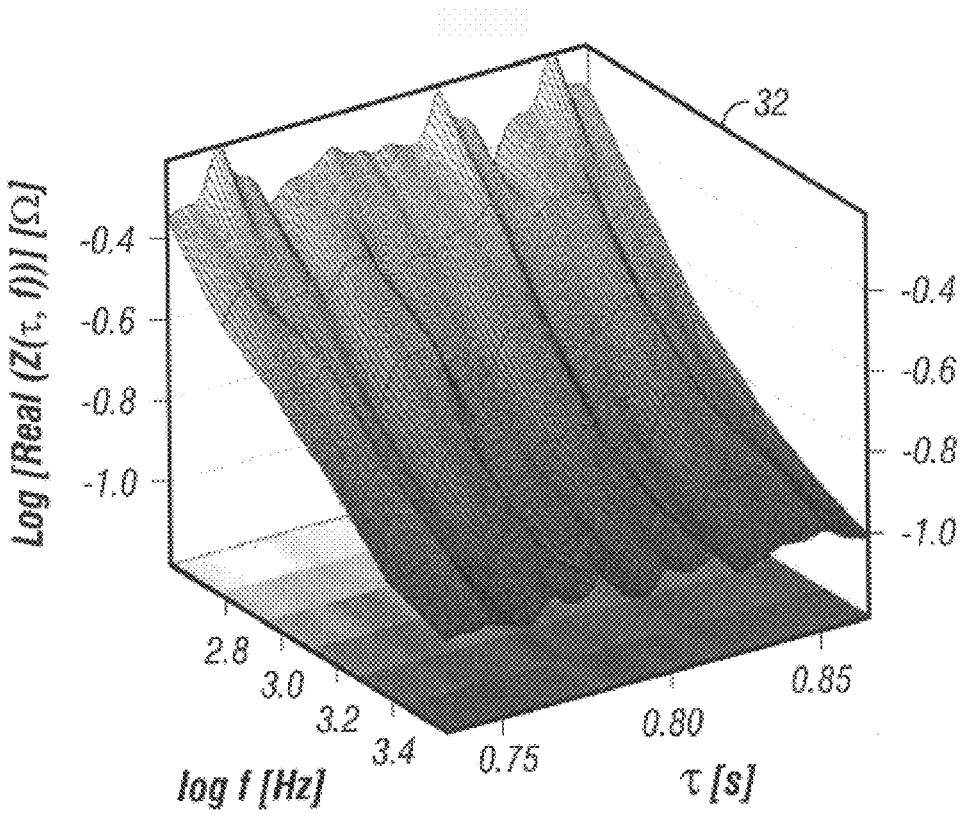
FIG. 3 is a plot illustrating examples of a sequence of impedance spectra as a function of the frequency f and the time t for a non-stationary system.

A method and apparatus to measure impedance and impedance spectra in rapid sequence thereby providing repeated or continuous characterization of the electrical properties of the system under investigation. Highly time resolved impedance spectroscopy is able to measure the dynamics of non-stationary systems with enhanced time resolution.

Three aspects of highly time resolved impedance spectroscopy are: (1) an optimized, frequency rich a.c., or transient, voltage signal is used as the perturbation signal; (2) non-stationary time to frequency transformation algorithms are used when processing the measured time signals of the voltage U(t) and current I(t) to determine a sequence of impedance spectra, where each spectrum is localized in time; and (3) the system-characterizing quantities are determined from the impedance spectra using equivalent circuit fitting in a time-resolution-optimized form.

Optimized Frequency Rich Perturbation Signal

The optimized frequency rich perturbation signal may be of many different formats. A frequency rich perturbation signal may contain any desired amount of contributing frequencies which are superimposed in one signal. For example, a frequency rich perturbation signal may be the superposition of a specific number of sinusoidal oscillations, or voltage jumps, pulses, and noise signals. The higher the signal to noise ratio of the voltage perturbation and the current response signal, the lower the time expansion of the database that is required to attain a certain measuring precision.

Structured noise may be used as the perturbation signal for highly time resolved impedance spectroscopy. Structured noise is defined as the superposition of a finite number of sinusoidal oscillations. FIG. 1 is a plot versus time of an example of a structured noise voltage signal U(t) (18). FIG. 2 is a power spectrum density plot of a structured noise voltage and current signals U(f) (20) and I(f) (22). The structured noise illustrated in FIGS. 1 and 2, can be represented mathematically by equation (2):

$$U(t) = \sum_{i=1}^{n} U_{0,i} \cdot \sin(\omega_i t + \varphi_i) \quad \text{with } 5 \leq n \leq 50 \qquad (2)$$

In equation (2), $U_{o,i}$ is the amplitude of the i-th sinusoidal oscillation with angular frequency $\omega_i$ and $\varphi_i$ is the phase. A favorable signal to noise ratio may be obtained when the perturbation signal U(t) is tuned, or optimized, to the system and the focus of measurement. Optimization of perturbation signals has been the subject of some research. See G. S. Popkirov and R. N. Schindler: "A New Impedance Spectrometer for the Investigation of Electrochemical Systems." Rev. Sci. Instrum. 63 (11), 5366–5372 (1992).; G. S. Popkirov and R. N. Schindler: "Optimization of the Perturbation Signal for Electrochemical Impedance Spectroscopy in the Time Domain." Rev. Sci. Instrum. 64 (11), 3111–3115 (1993). All the above publications are incorporated by reference in their entirety herein.

Numerous optimization steps are an aspect of highly time resolved impedance spectroscopy including: the frequency band in which the impedance is measured; the number and frequency, amplitude and phase of the individual contributing frequencies.

Optimization of the perturbation signal includes selection of the frequency band in which the impedance spectrum is measured. Therefore, the frequency band of the perturbation signal should be selected to include the maximum spectral range to be covered by the measurement. However, when evaluating the impedance spectra one can use just selected frequencies of the n frequencies in the perturbation signal. This aspect is discussed further below.

Optimization of the perturbation signal may also include selecting a desired number (n) and frequency position ($\omega_i$) of the n individual contributing frequencies. Any desired number and frequency positions of the individual frequencies can be used. This maximizes for the user the adaptability of the high time resolution impedance spectrometer to the system under investigation.

In one embodiment, the power applied by a structured noise signal to the sample depends on the number of the frequencies in the noise signal. Because many systems exhibit linear behavior only with small amplitude or low power perturbation, it is desirable to keep the number of frequencies as low as possible. On the other hand, the reproduction of the characteristic system response requires a minimum number of frequencies in the impedance spectrum. Because in impedance spectroscopy the impedance is usually determined over several orders of magnitude of the frequency, a desired number of individual frequencies per frequency decade is selected, if special system requirements do not require deviating from this desired number. In one embodiment, five individual frequencies per frequency decade is a suitable number.

In one embodiment, the distribution of the frequency position of the individual frequencies is selected in a logarithmic uniform distribution over the entire frequency band. In another embodiment, the distribution of the frequency position of the individual frequencies selected is varied from a logarithmic uniform distribution in a manner to avoid the formation of harmonics. Preventing harmonics helps to prevent the corruption of the measured impedance spectra by nonlinear system responses or the excitation of higher harmonics.

Another aspect of the perturbation signal that may be optimized is the amplitude $U_{o,i}$ of the individual frequencies. Any desired amplitude of the individual frequencies may be selected. In one embodiment, to optimally exploit the linear range of a measuring amplifier, and attain an optimum signal to noise ratio for each frequency in the system, the amplitudes of the individual frequencies are adapted to the measuring situation. In one embodiment the amplitudes of the individual frequencies in the perturbation signal are such that the power of the individual frequencies in the perturbation signal is constant (good for use with strongly non-linear systems). In another embodiment the power of the current response of the excited individual frequencies is constant (reduction of the influence of non-linearity of the measuring amplifier, see FIG. 2). In yet another embodiment, the power of the individual frequencies of the perturbation signal and the current response reveals minimal differences (optimum signal to noise ratio).

Yet another aspect of the perturbation that may be optimized is the phase $\omega_i$ of the individual frequencies. Any desired phase angle of the individual frequencies may be selected. In one embodiment, a linear system response maybe ensured by the lowest possible overall amplitude of the perturbation signal. The phases of the individual frequencies in the structured noise are selected so that the overall amplitude of the signal is minimal while the amplitudes of the individual frequencies remain the same. Hence the power of the individual frequencies is retained despite reduced overall amplitude, or the power of the individual frequencies is maximized and the signal to noise ratio is improved, as the overall amplitude remains fixed.

Non-Stationary Time to Frequency Transformation Algorithms

An aspect of highly time resolved impedance spectroscopy is the determination of impedance spectra, which are localized in time, with reduced averaging time in high repetition rate. Non-stationary time to frequency transformation algorithms are used in highly time resolved impedance spectroscopy. The averaging time corresponds to the prolongation of the database that is required for determining an individual impedance spectrum. Sequences of spectra $X(\omega)$, which are localized in time, are determined from the time signals $X(t)$ by applying window functions spanning a small period of time of the measuring signal $X(t)$ (either U(t) or I(t)) and repeating this procedure, applying window functions shifted by brief, or short, intervals. The time signals, including the a.c. voltage signal U(t) applied to the sample and the current response I(t) of the sample, are continuously or partly continuously recorded over a given period only limited by the storage capacity of the used data storage media. A partly continuously recorded data set may be defined as a repeated recording of finite data sets of any length with arbitrary, or selected, interruption intervals between consecutive data sets.

Examples of non-stationary, time to frequency transformation procedures include sliding short time Fourier transform, wavelet transformation and Wigner or Wigner-Ville distribution. Two of these methods will be described further below: (1) sliding short time Fourier transform; and (2) wavelet transformation.

In sliding short time Fourier transform the time to frequency transformation is carried out corresponding to the formula for continuous short time Fourier transform:

$$\hat{X}(\iota,\omega) = \int x(t)g^*(t-\iota) \cdot e^{-1\omega t} dt \qquad (3)$$

In equation (3) x(t) corresponds to the measured time signal, g(t) is a window function whose characteristic is adjusted to optimize the spectrum X(ι,ω) that is obtained as a result of the transformation step. See L. Cohen: *Time-frequency Analysis* (Prentice Hall PTR, Englewood Cliffs, N.J., 1995) incorporated by reference in its entirety herein. Various possible window functions have been described. See F. J. Harris: "On the Use of Windows for Harmonic Analysis with the Discrete Fourier Transform." Proceedings of the IEEE 66 (1), 51–83 (1978) incorporated by reference in its entirety herein.

The resulting impedance spectrum Z(ι,ω) is obtained according to equation (1) from the quotients of the spectra of the voltage signal U(ι,ω) and the current signal I(ι,ω). This impedance spectrum is assigned to the time ι, that is, it characterizes the investigated sample at time ι of the measurement. The spectral information is hence localized at time ι by considering, and weighting, only a section of the overall data record around time ι for the time to frequency transformation. The impedance spectrum yields the complex impedance depending on the angular frequency ω=2*π*f where f is the frequency. A sequence of impedance spectra is obtained by repeatedly calculating impedance spectra according to the described procedure where the time ι shifts by interval Δι for each of the subsequent spectra.

Figure 3B:
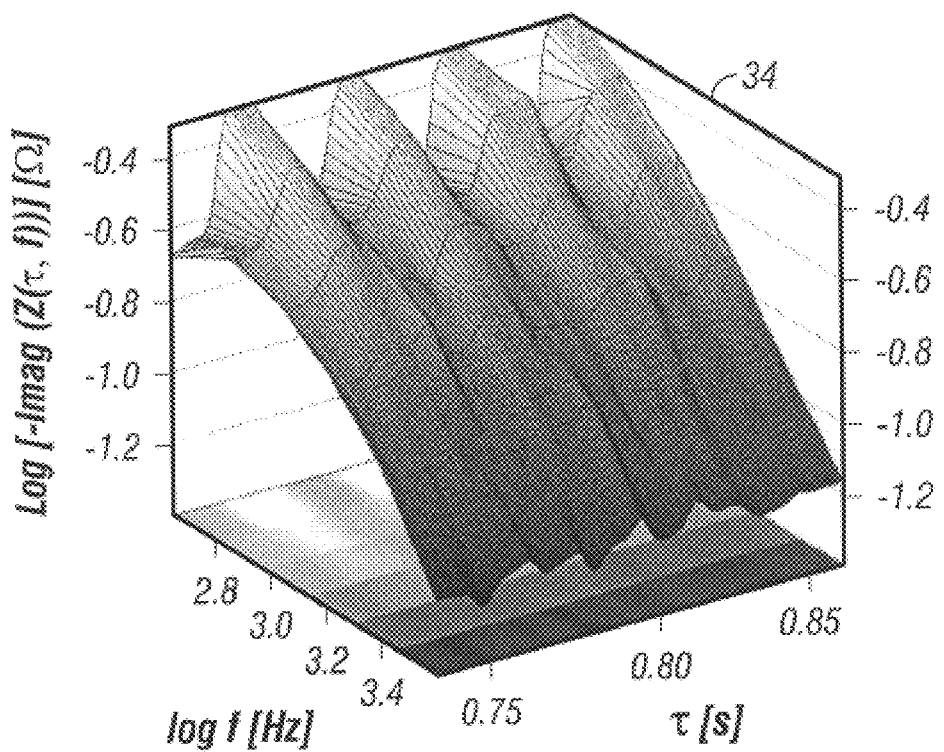

FIG. 3 is a plot illustrating examples of a sequence of the real (32) and imaginary (34) impedance spectra as a function of the frequency f and the time ι for a non-stationary system. In the manner described above, the measured data records are completely analyzed when ι is shifted as much as possible by interval Δι in the data record from the start of measurement. If the interval Δι is smaller than the prolongation of the window function g(t), one speaks of sliding short time Fourier transform since the window functions g(t-ι) applied to the data records overlap within the sequence. The interval Δι in which the window function shifts between each transformation, defines the time resolution of the procedure.

To attain a high time resolution, Δι must be correspondingly small. Likewise, the time over which g(t) is not zero must be as small as possible to reduce the time averaging in the time to frequency transformation. The window function g(t) defines the maximum peak-to-peak resolution $\Delta t_{pp}$ of short time Fourier transform provided by the expression:

$$\Delta t_{pp}^2 = \frac{\int t^2 |g(t)|^2 dt}{\int |g(t)|^2 dt} \qquad (4)$$

When the measured data records of U(t) and I(t) exist in discrete form, for example, in the case of computer-supported, or digitized, data acquisition, the discrete algorithm of the short time Fourier transform of equation (5) is used instead of continuous short time Fourier transform.

$$\hat{X}_d(\tau,\omega) = \sum_{n=0}^{N-1} x(nT_a)g^*(nT_a - \tau) \cdot e^{i\omega nT_a} \qquad (5)$$

$T_a$ is the sampling interval for data acquisition, n the running variable for the number of observed data points, and N the total number of data points. All other quantities correspond to the definition in continuous short time Fourier transform. The shift interval Δι typically is a whole-number multiple of $T_a$. The frequency resolution Δf and the upper frequency limit $f_{max}$ in each impedance spectrum are subject to the sampling theorem expressed in equation (6). See E. Schrüfer: *Signalverarbeitung*. (Hanser, Munich: 1990), incorporated by reference in its entirety herein.

$$\Delta f = \frac{1}{N_w \cdot T_a} \text{ and } f_{max} = \frac{1}{2 \cdot T_a}. \qquad (6)$$

where $N_W$ is the number of data points above which the window function $g(nT_a)$ is not zero.

In wavelet transformation the time to frequency transformation is carried out corresponding to the formula of continuous wavelet transformation:

$$\tilde{X}(\tau,s) = \frac{1}{\sqrt{|s|}} \int x(t) \cdot h^*\left(\frac{t-\tau}{s}\right) dt. \qquad (7)$$

See O. Rioul and M. Vetterli: "Wavelet and Signal Processing" in *Signal Processing Technology and Applications*. Edited by J. G. Ackenhusen (The Institute of Electrical and Electronics Engineers, Inc., New York: 1995) p.85–109 incorporated by reference in its entirety herein.

Instead of the variable of the angular frequency ω, the scale s is normally used for wavelet transformation. This is due to the fact that the pulse responses of the used wavelet functions $h_s(t)$ scales with s as e.g. is the case with a basic or prototype wavelet of the formula:

$$h_s(t) = \frac{1}{\sqrt{|s|}} h\left(\frac{t}{s}\right) \qquad (8)$$

One possible form for the window function h(t) is a modulated window function g(t) as is used in short time Fourier transform:

$$h(t) = g(t)e^{-1\omega_0 t}. \qquad (9)$$

In equation (9), $\omega_0$ corresponds to the modulation frequency of the basic, or prototype, wavelet. By scaling the basic function for the time to frequency transformation, the time resolution is not set for the entire spectrum but varies with the analyzed frequency or scale. This has an advantage that the time averaging is reduced by the time to frequency transformation at high frequencies by reducing the database. This increases the time localization and permits a substantially higher time resolution at this range. In addition, the considered database at low frequencies is expanded so that the contribution of these frequencies can be integrated into the spectral information. Overall, the information content of the determined sequence of impedance spectra may be greatly increased. The time resolution can be optimally adjusted by selecting the suitable shift interval Δι for a sequence of impedance spectra obtained by wavelet transformation, for either the entire frequency bandwidth or just selected frequencies of interest.

In the case of discrete data records, a corresponding algorithm is used for discrete wavelet transformation or wavelet series expansion.

The highly time resolved impedance spectroscopy offers many advantages over conventional impedance spectroscopy including the use of reduced impedance spectra. The impedance spectra obtained by short time Fourier transformation, e.g. intrinsically includes $N_W/2+1$ frequencies which can be reduced to the n frequencies that are contributing to the structured noise. Because the discrete algorithms only provide impedance values for discrete equidistant frequencies, frequencies are selected that are closest to the excited frequencies. This step eliminates most of the background noise of the measurement from the impedance spectra. Only the frequencies with the best signal to noise ratio are contributing to the impedance spectra, allowing the use of window functions which span a smaller period of time, resulting in a lower averaging time for the spectral information.

Equivalent Circuit Fitting in a Time-Resolution-Optimized Form

After determining the reduced impedance spectra, the spectra may be analyzed by adapting suitable equivalent circuit models to determine the system-characteristic quantities and their time course. The elements that compose the equivalent circuits are derived from physical models for the dominant processes occurring in the system and frequently correspond to the behavior of ideal electrical components such as resistors, capacitors and inductors. In the impedance spectrum, distinct processes dominate the impedance response of the system in different ranges of frequencies. In highly time resolved impedance spectroscopy, either the measured and reduced impedance spectra are evaluated completely or in certain ranges of the spectra. In principle, you can determine whether or not each frequency contributing to the reduced impedance spectrum is used for evaluation.

An advantage of highly time resolved impedance spectroscopy is the possibility of multiple analyses of the same data records with different analysis parameters, e.g. time resolutions $\Delta t$. For the multiple analyses of data records, first impedance spectra are determined with a longer window function leading to a long averaging time and a low time resolution, and therefore the reduced impedance spectra can be evaluated completely. The parameters of the stationary, i.e., constant processes are hence determined with a high degree of precision.

The impedance spectra with a shorter window function, leading to a short averaging time and high time resolution, are determined in another analyses of the same data records. When the spectra are evaluated, only the areas of reduced spectra are used that characterize the dynamic non-stationary processes, and the parameters for the static or stationary processes. in the equivalent circuit are set to the previously-determined values.

The complex impedance values can be represented in different forms. For example, the impedance can be represented by complex coordinates or polar coordinates:

$$Z(\omega)=Re[Z(\omega)]+i\cdot IM[Z(\omega)]=Z_0(\omega)\cdot e^{i\phi(\omega)}. \tag{10}$$

Likewise, the reciprocal impedance (termed admittance) or related quantities can be used such as the complex frequency-dependant dielectric constant in both coordinate forms. The significance of individual processes in certain frequency ranges of the impedance spectra varies with the coordinate form used. For analysis, highly time resolved impedance spectroscopy may use the electrical variables and coordinate form that significantly resolve the non-stationary processes in the highest frequency range. The higher the frequencies at which the investigated processes can be analyzed allows for the selection of a smaller time period spanned by the window functions and a smaller shift interval $\Delta t$ for use in the sliding short time Fourier transform.

For example, a method for adapting the parameters of the equivalent circuit to the measured impedance spectra includes complex non linear least square fitting methods. A problem of the minimization algorithm for adapting the equivalent circuit to the impedance data (e.g. Levenberg-Marquardt, Powell's minimization method in multidimensions) is that the algorithm frequently finds local minimums instead of the global minimum in the fitting. See W. H. Press, S. A. Teukolsky, W. T. Vetterling et al. *Numerical Recipes in C* (Cambridge University Press, New York, 1992) incorporated by reference in its entirety herein.

To increase the probability of determining the global minimum in the fitting, different coordinate forms and variables can be combined. In highly time resolved impedance spectroscopy, sequences of impedance spectra may be evaluated by an automatic fitting routine or process. As a result, the time courses of the system-characterizing quantities are determined.

The procedure described above is not limited to electrical impedance and can be used to determine mechanical impedance spectra such as in rheological measuring methods, magnetic and optical tweezers, quartz resonance balances and acoustic impedance measurements as well as other procedures in which the frequency rich perturbation of a system is related to the system response.

EXEMPLARY EMBODIMENT

One embodiment will be described in detail to assist in understanding various aspects of highly time resolved impedance spectroscopy. Although one embodiment is described in detail, highly time resolved impedance spectroscopy may be embodied in other specific forms without departing from its spirit or essential characteristics. The embodiment describes a scenario that would facilitate the measurement, or determination, of the impedance of individual ion channels in supported lipid membranes, biomembranes. In another embodiment, the impedance of natural or artificial, freely-suspended or substrated supported lipid membranes with or without ion channels may be measured. The substrates bear planar thin-film microelectrodes that are in multiple electrode arrangements, facilitating parallel and sequential multiplex measurements on the substrate. The substrates can be fabricated from, for example, silicon substrates with metal or semiconductor electrodes. The substrates may be mounted in an electrochemical cell, of either one or multiple measuring chambers, in which liquid can be exchanged by a manual, or automated, liquid handling and control system 64 (FIG. 5) with or without temperature control. Such a scenario corresponds to the measurement of an electrical two-terminal network that is simplified by the circuit depicted in FIG. 4.

Figure 4:
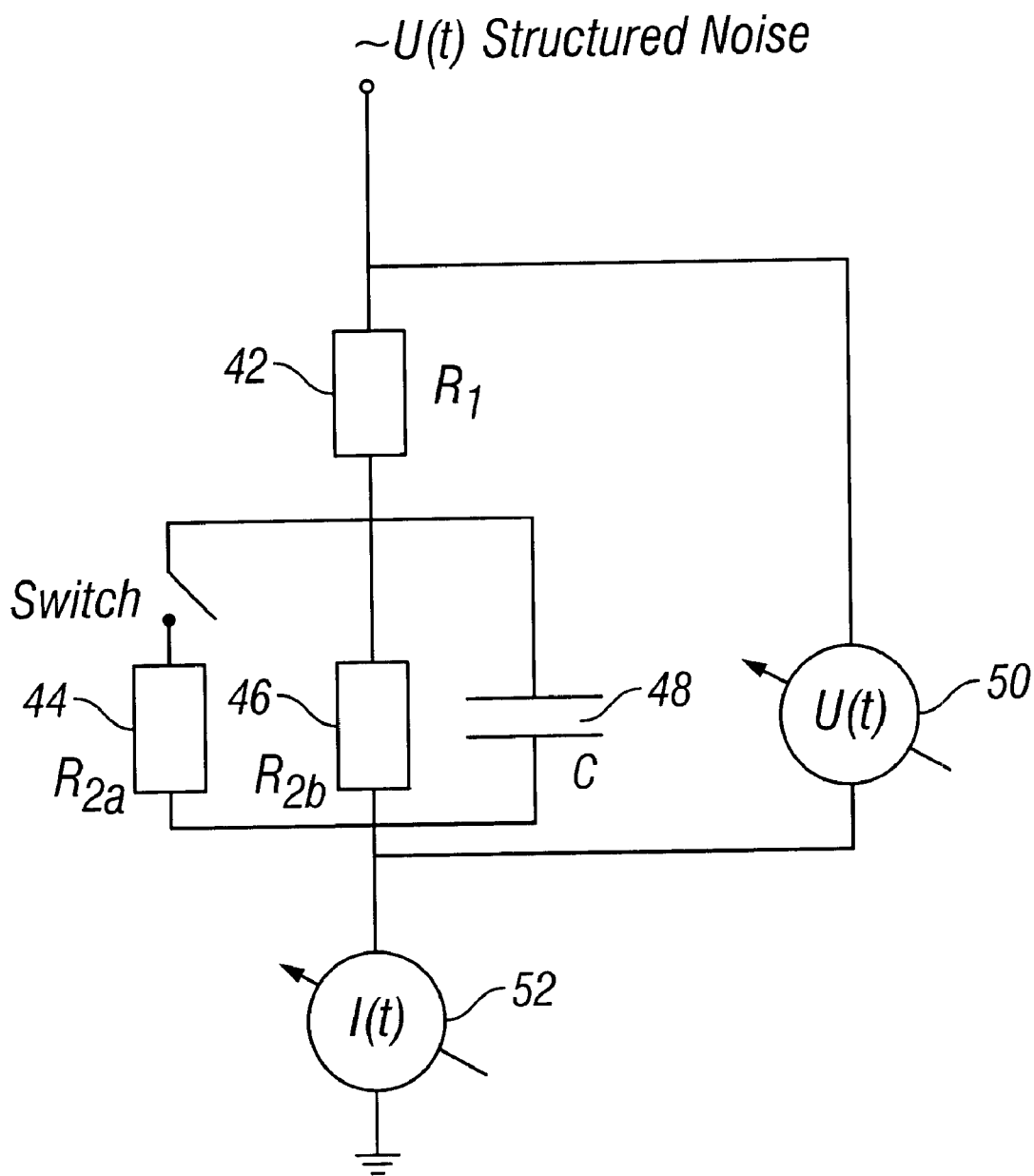
FIG. 4 is a schematic of an equivalent circuit.

FIG. 4 is a schematic of a typical equivalent circuit. The typical equivalent circuit of FIG. 4 has a resistor $R_1$ (42) in series with the paralleled combination of resistor $R_{2a}$ (44), $R_{2b}$ (46) and C (48). A switch is in series with $R_{2a}$ (44). The excitation voltage U(t) (50) is measured across the equivalent circuit, and the response current I(t) (52) flowing through the circuit is measured. Typical values of the components can be assumed to range from $R_1 \sim 100$ k$\Omega$, $R_{2a,2b} \sim 1$ G$\Omega$ and C~6 pF. Switching rates for the switch can be assumed to be e.g. 50 Hz.

Figure 5:
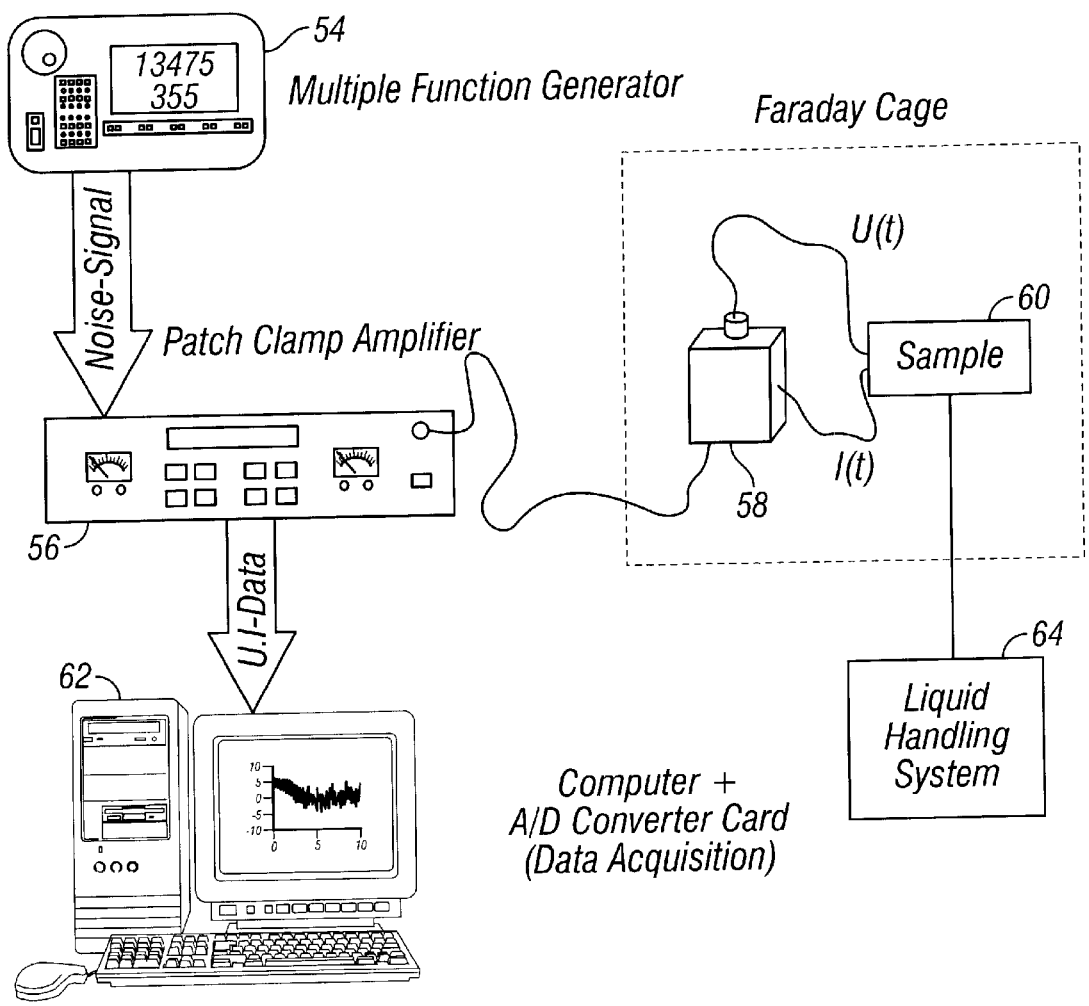
FIG. 5 is a block diagram representation of one embodiment of a highly time resolved impedance spectroscopy system.

FIG. 5 is a schematic representation of one embodiment. A structured noise of the a.c. voltage perturbation signal was calculated by a computer and sent to the memory of the multifunctional generator (54) (Analogic® 2030A). This device generates the perturbation signal and feeds it into the patch clamp amplifier (56) (HEKA® EPC8).

When digital data records are used for the perturbation signal, the transitions between the discrete voltage steps should be small and smoothed because this reduces the level of background noise of the perturbation signal. In order to have small steps between two consecutive values of the perturbation signal, the sampling rate at which the data record is output by the function generator should be greater by a factor of about ten than the largest frequency of interest in the impedance spectra.

To smooth the discrete steps, the perturbation signal can be filtered with a lowpass filter, with the corner frequency of the filter greater by a factor of about ten above the highest frequency of interest in the impedance spectra. The patch clamp amplifier (56) transmits the a.c. voltage perturbation signal via an external preamplifier (58) to the sample (60) under test. This preamplification unit simultaneously measures the actual a.c. voltage applied to the sample and the current response of the sample. The current signal is filtered, amplified and undergoes current to voltage conversion. Both time signals U(t) and I(t) can be monitored as voltage signals at the corresponding outputs of the patch clamp amplifier (56). Both signals are acquired by two channels of the A/D converter board (National Instruments Lab-NB) in a measuring computer (Apple Macintosh IIfx) and saved in data records on the computer data storage media.

The software necessary to operate the setup includes two programs. The first program performs the data acquisition on the measuring computer with the A/D converter board. It includes the data analysis software Igor Pro® (WaveMetrics) with an expansion package for data acquisition (NIDAQ Tools). The second program performs the signal processing and data analysis of the measured data records of U(t) and I(t). It is a custom-written C++ program for Macintosh and Windows operated PCs. The implemented algorithm of the sliding short time Fourier transform is based on a modified Cooley-Tukey FFT algorithm.

To fit the equivalent circuits to the impedance spectra, a modified minimizing algorithm was derived from the method of Powell in multidimensions. For the above-specified application, the logarithms of the real part and the negative imaginary part of the impedance spectra (complex coordinates) were used for the data fitting by the minimization procedure. See W. H. Press, S. A. Teukolsky, W. T. Vetterling et al. *Numerical Recipes in C* (Cambridge University Press, New York, 1992).

The performance characteristics of the described embodiment were quantified in simulations and test measurements. For the simulations, the corresponding current response signals of an ideal system were calculated by the computer for the structured noise perturbation signals, and the generated signals U(t) and I(t) were evaluated using the signal processing and data analysis procedure of highly time resolved impedance spectroscopy. FIG. 6 is a table that shows examples of parameters for the structured noise signal (66) and data processing (68) in the "Simulations" column. The simulations demonstrate that a membrane/ion channel system with characteristic quantities $R_1$=100 k$\Omega$, $R_2$ switching between distinct values in a range of 0.8–20 G$\Omega$ and C=6 pF can be measured correctly by using the logarithms of the complex coordinates in a minimization procedure even in a narrow frequency band of 0.3–20 kHz with only six individual frequencies. In general, for the analysis of impedance spectra of membrane ion channel systems a frequency band of 100 Hz to 100 kHz may be used.

The equivalent circuit of the membrane/ion channel system is provided by FIG. 4, where the combination of $R_{2a}$ and $R_{2b}$ is considered as $R_2$.

Figure 7:
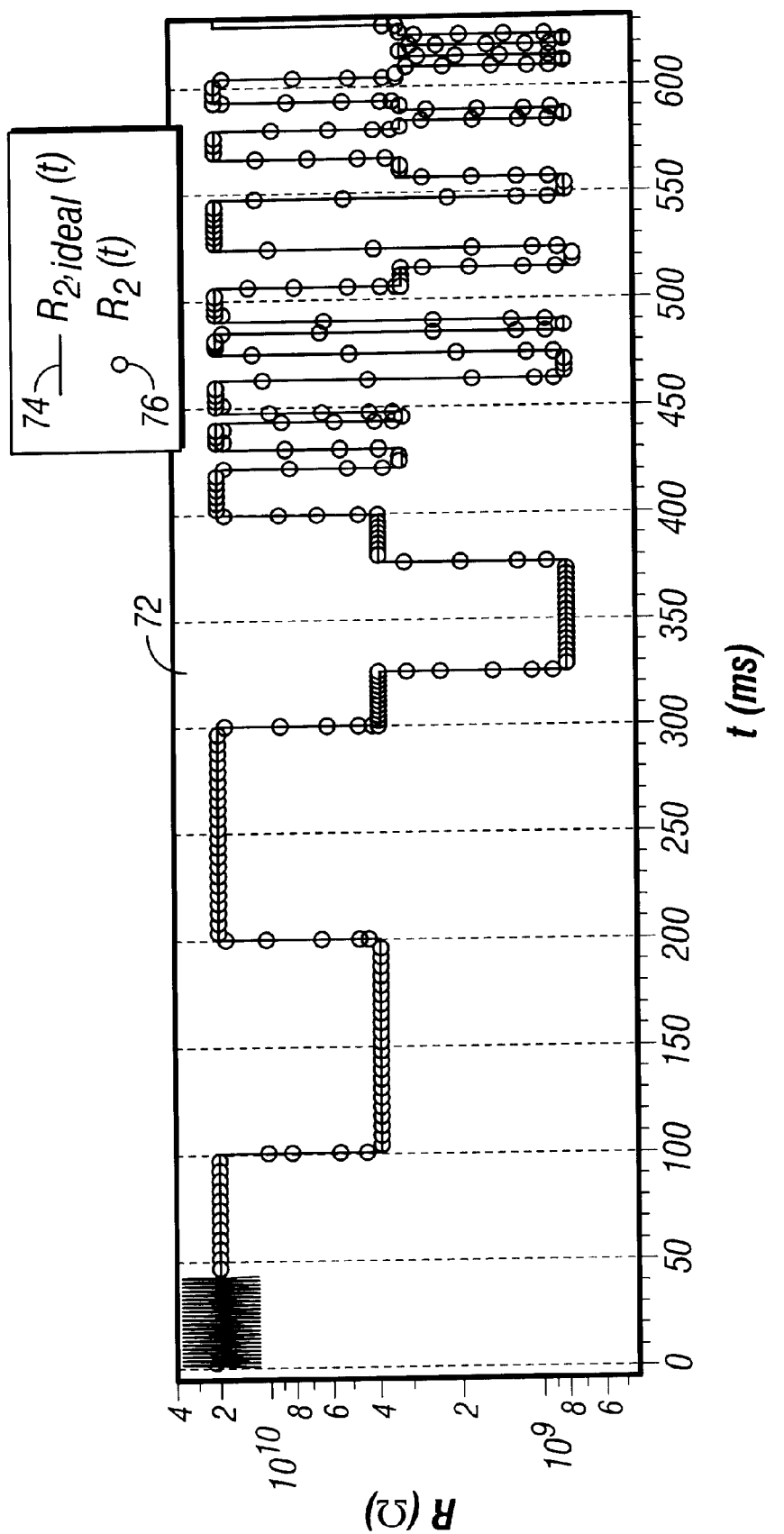
FIG. 7 is a graph illustrating an example of the time course of the resistance $R_2$ of the non-stationary system of FIG. 4 (simulation).
Figure 8:
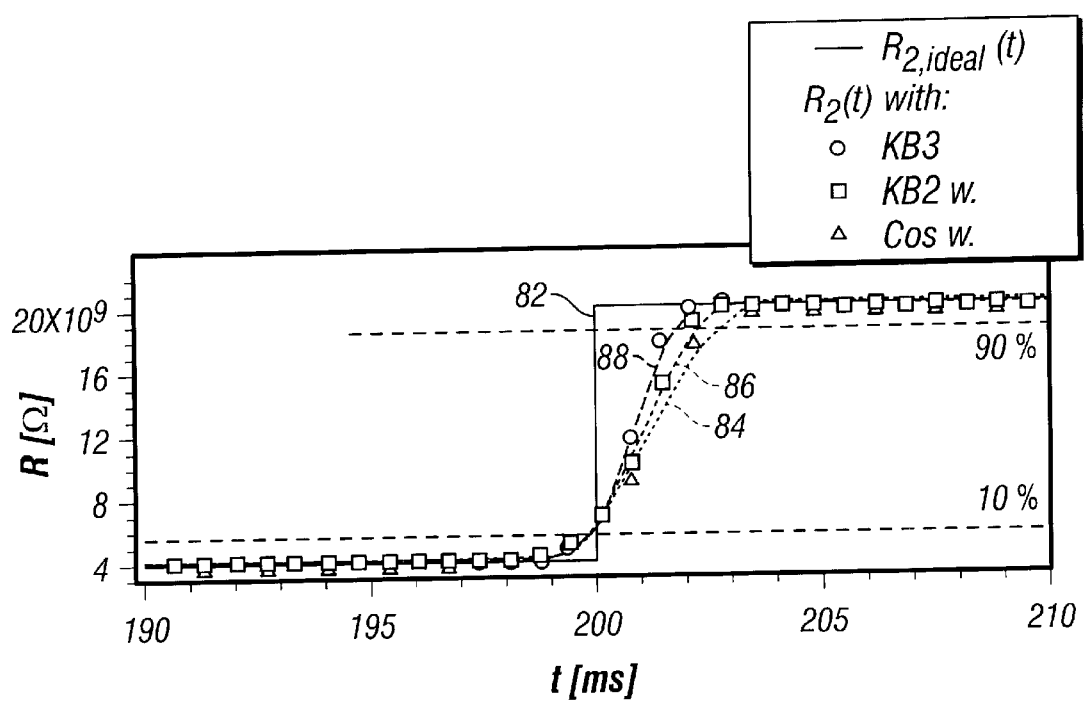
FIG. 8 is a graph of an expanded portion of FIG. 7 illustrating a transition in the value of $R_2$.

In FIG. 7 the time course (72) of the switchable parallel resistor $R_2$ is shown as it was assumed for the simulation (74) (continuous line) and as determined by highly time resolved impedance spectroscopy (76) (circle). FIG. 8 shows one jump (82) in $R_2$ enlarged from FIG. 7. The different curves shown result from using different window functions g(t) in the short time Fourier transform. Window functions of the following characteristics were used: Hanning 1.0 (Cos.) (84), Kaiser-Bessel with $\alpha$=2.0 (KB2) (86), and Kaiser-Bessel with $\alpha$=3.5 (KB3) (88). The analysis of the time course reveals, that in the absence of any signal corruption, the time course of the system-characterizing quantities determined by the short time Fourier transform corresponds to the convolution of the real (ideal) time course of this quantity with the window function used. The time resolution attained was $\Delta t$=0.67 ms, and the rise time $t_r$ was between 2.0 and 3.1 ms depending on the window function.

For the test measurements, the circuit in FIG. 4 was assembled by using electronic components. Such a circuit forms a model sample, which mimics the behavior of individual ion channels in supported lipid membranes. These model samples were measured by highly time resolved impedance spectroscopy.

In a first test measurement, a model was used with the values of $R_{2a,2b}$=680 K$\Omega$ and C=1 nF (no additional element for $R_1$), and the switch was switched at a frequency of 50 Hz. FIG. 6 shows the parameters of the structured noise signal and the data evaluation in the column, "fast model." In FIG. 9 the time courses of $R_1$ (92), $R_2$ (94) and C (96) are shown as determined with highly time resolved impedance spectroscopy, as well as an ideal or absolute time course of $R_2$ (98).

Figure 9:
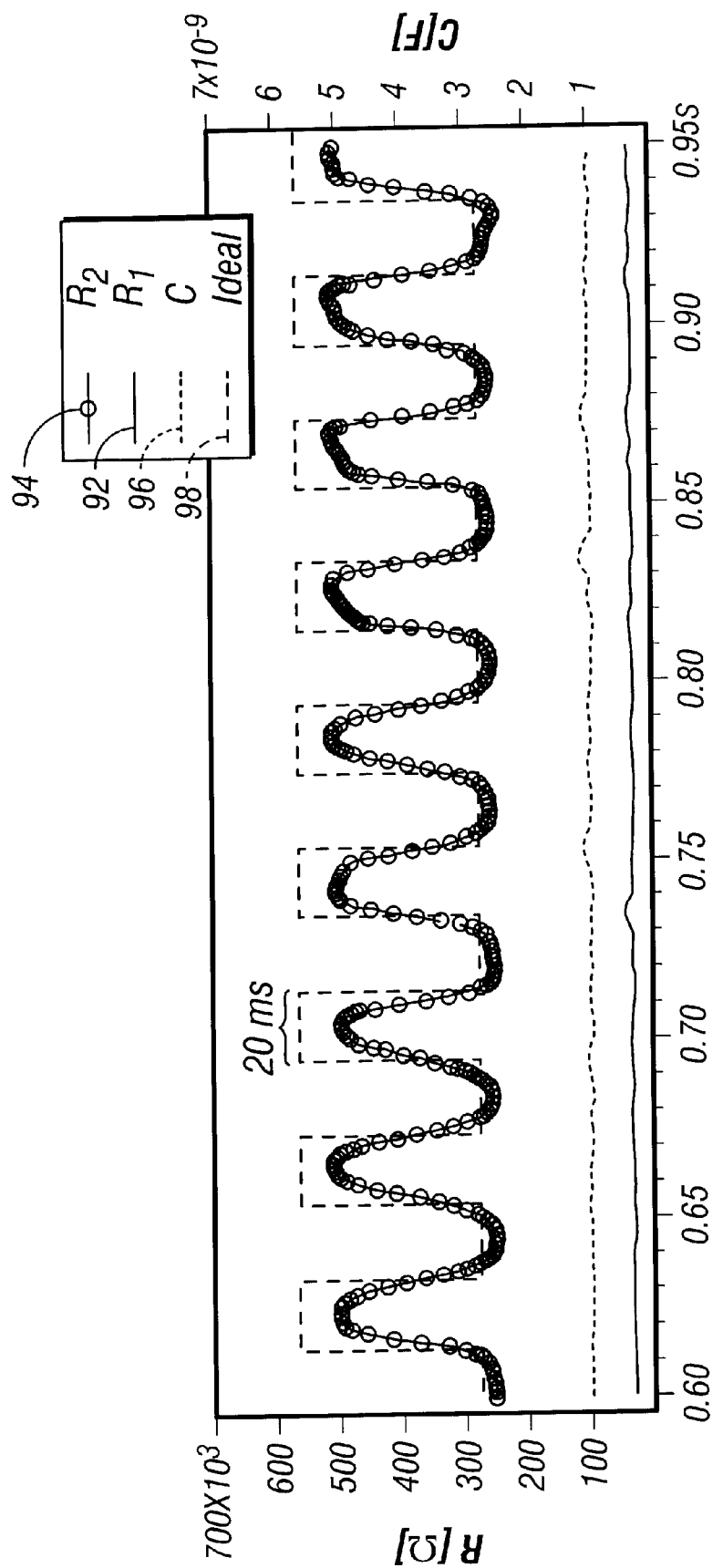
FIG. 9 is a graph illustrating an example the time course of the values of the equivalent circuit elements of FIG. 4 measured with highly time resolved impedance spectroscopy.
Figure 10A:
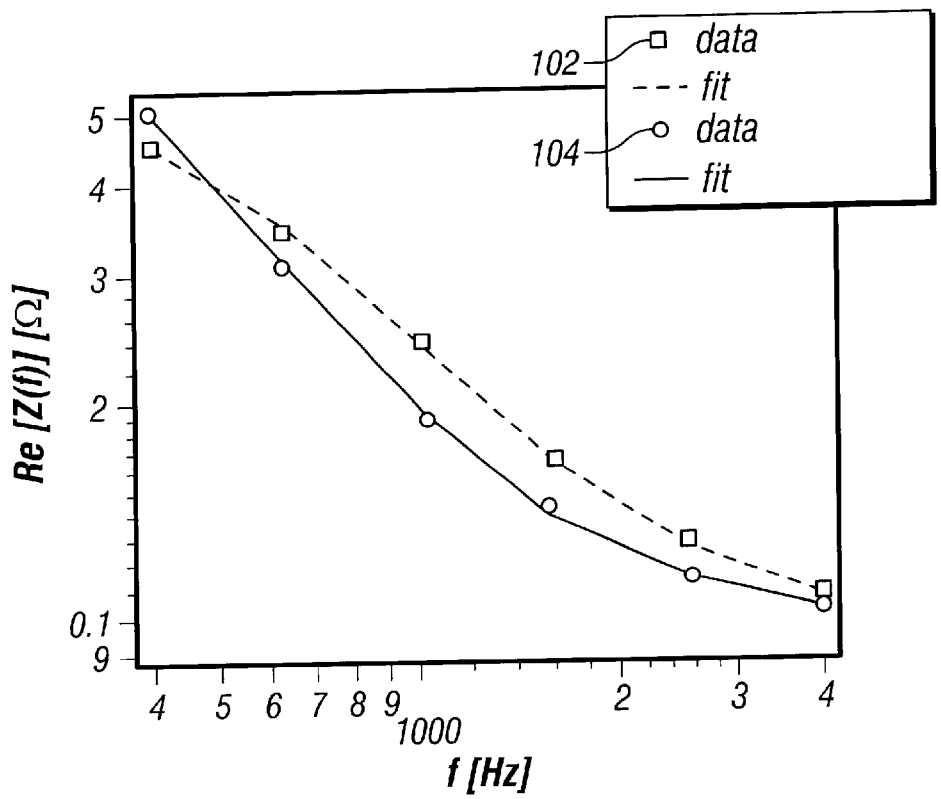
FIG. 10(a) is a graph illustrating an example of the real part of the underlying impedance spectra for two points in the time courses in FIG. 9.
Figure 10B:
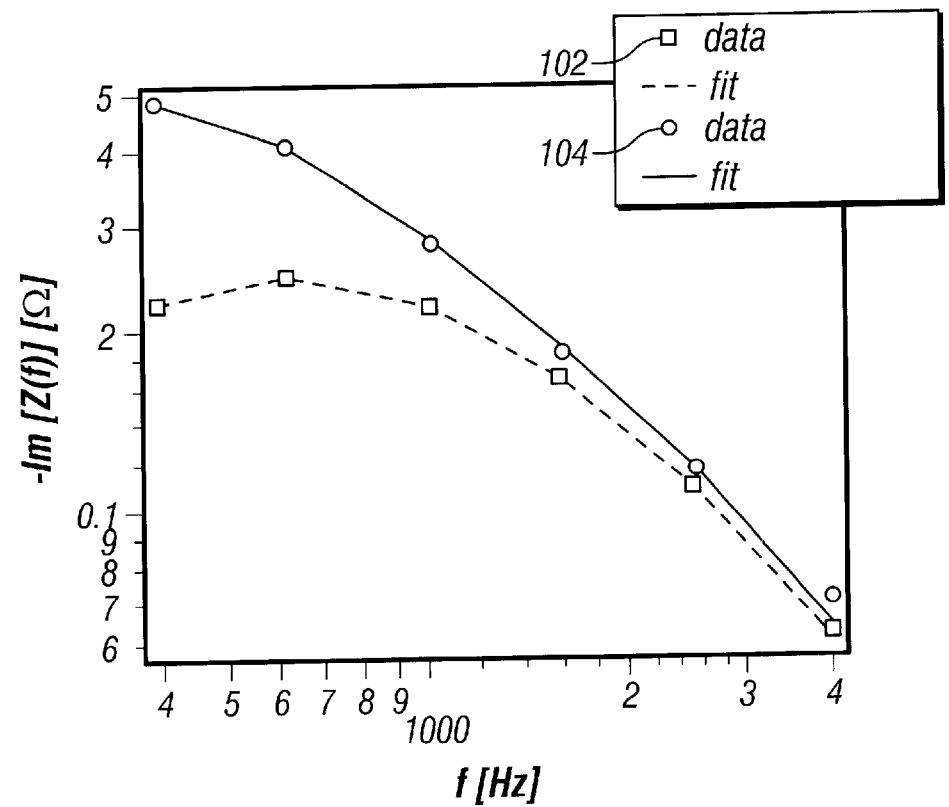
FIG. 10(b) is a graph illustrating an example of the imaginary part of the underlying impedance spectra for two points in the time courses in FIG. 9.

Deviations from the absolute values of up to 20% result from the insufficiently compensated filter effects of the setup. The step-like changes of $R_2$ are reproduced well. The attained time resolution was 1.1. ms, and the rise time was 8 ms. In FIGS. 10(a) and (b) the real and negative imaginary part respectively of the underlying impedance spectra (112) and (104) for two points in the time courses of FIG. 9 are shown. Not each of the contributing frequencies of the structured noise signal was used for the evaluation but just the limited range of 0.4–4 kHz.

Figure 11:
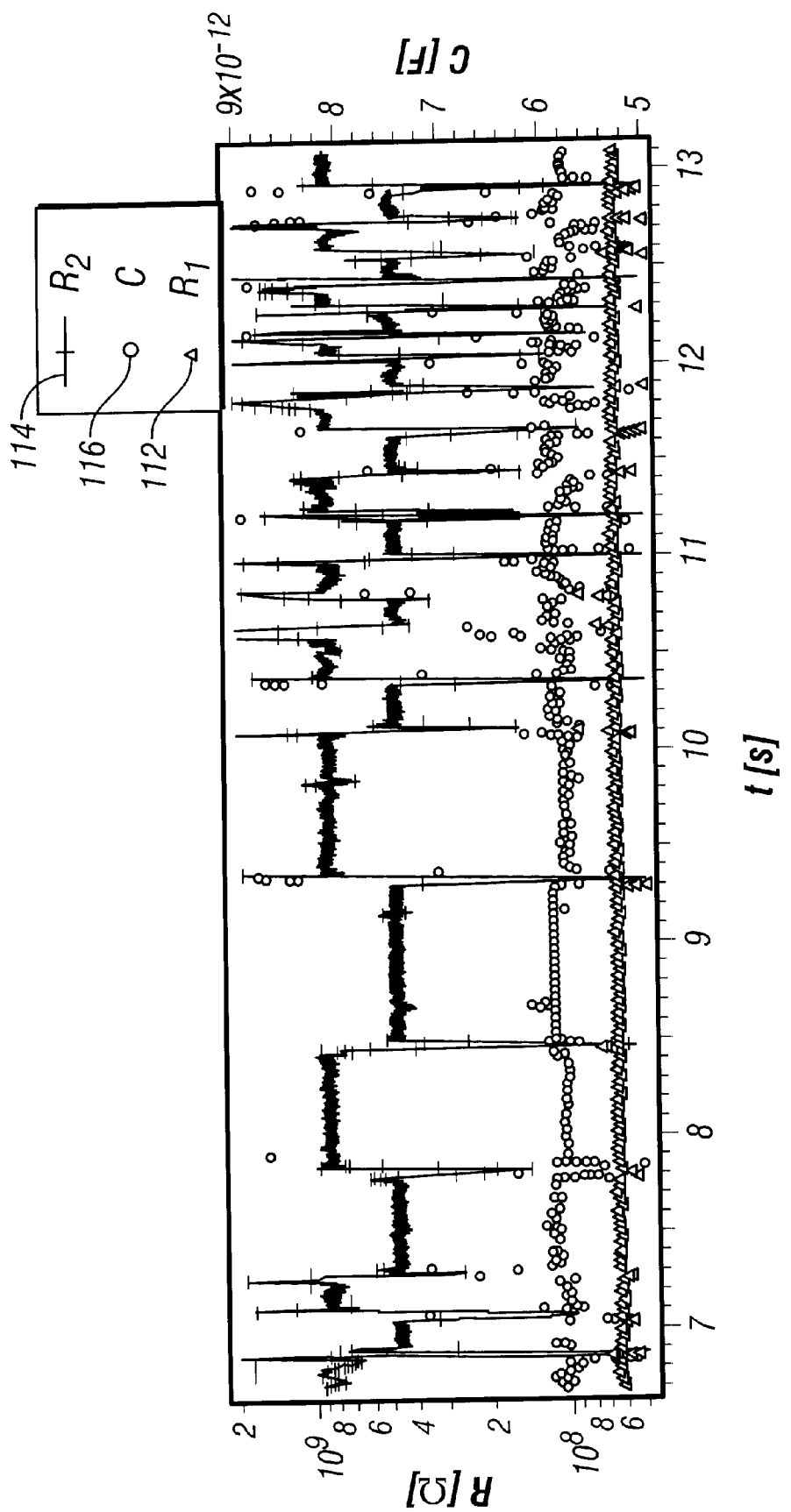
FIG. 11 is a graph illustrating an example of the time course of the values of the equivalent circuit elements of FIG. 4, measured with highly time resolved impedance spectroscopy.
Figure 12A:
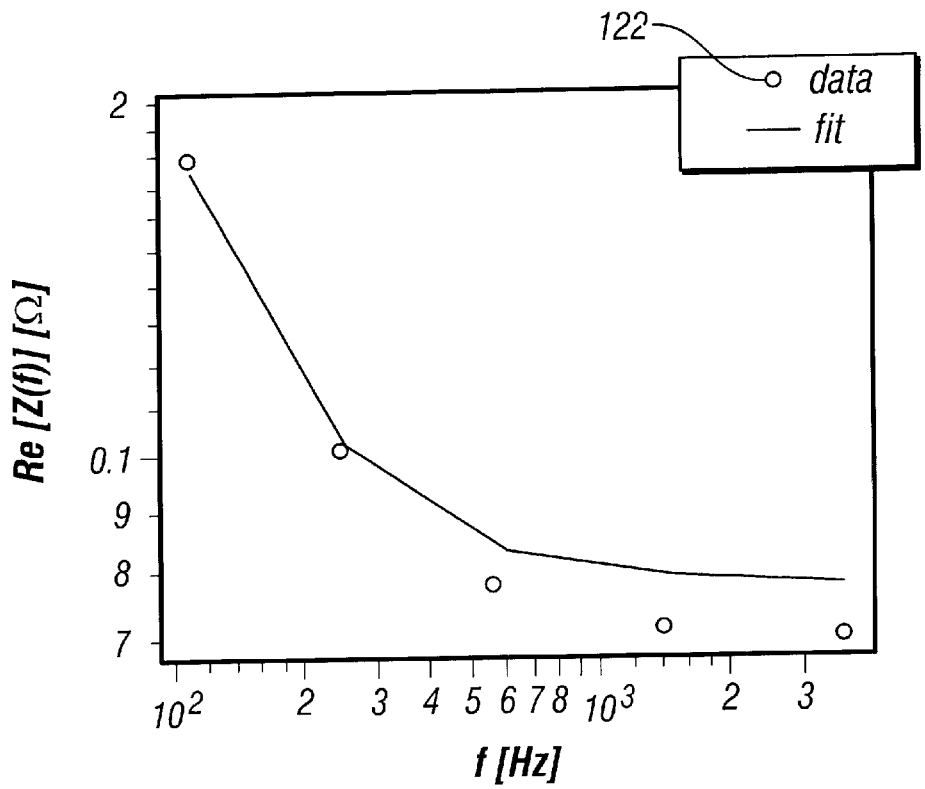
FIG. 12(a) is a graph illustrating an example of the real part of the underlying impedance spectrum for one point in the time courses in FIG. 11.
Figure 12B:
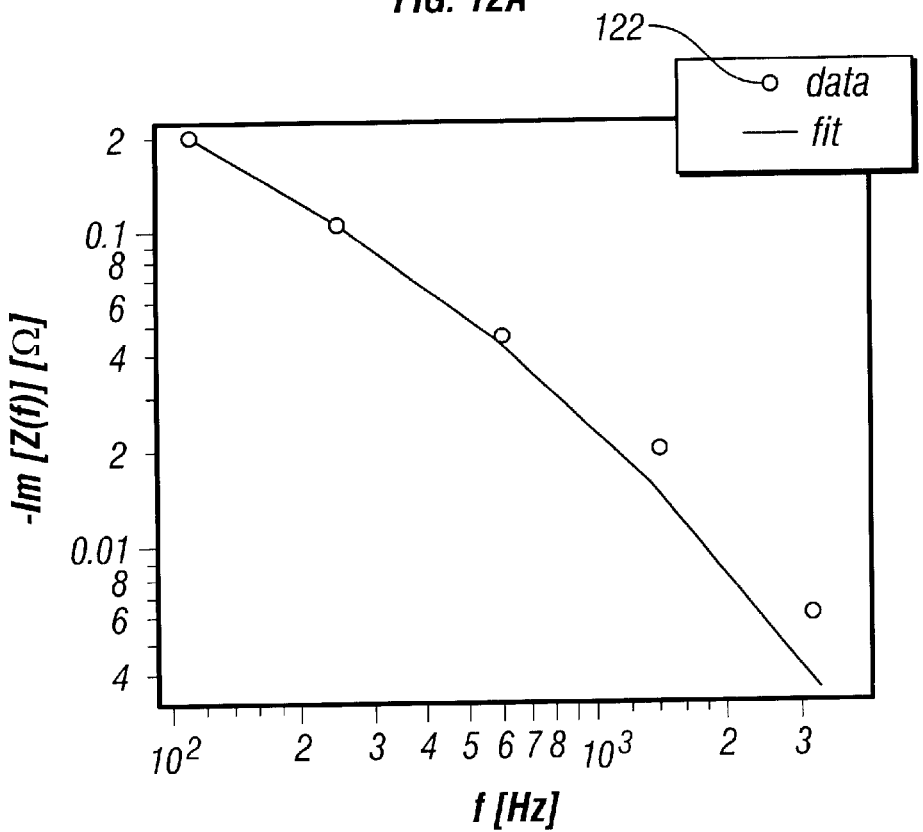
FIG. 12(b) is a graph illustrating an example of the imaginary part of the underlying impedance spectrum for one point in the time courses in FIG. 11.

In a second test measurement, a model was used with the values of $R_{2a,2b}$=1 G$\Omega$ and C=3 pF (no additional element for $R_1$), and the switch was switched manually at irregular intervals. FIG. 6 shows the parameters of the structured noise signal and the data evaluation in the column "Gigaohm Model." In FIG. 11 the time courses of $R_1$ (112), $R_2$ (114) and C (116) as determined by highly time resolved impedance spectroscopy are shown. Again, deviations from the absolute values of up to 20% result from the insufficiently compensated filter effects of the setup. The step-like changes of $R_2$ are clearly resolved also at these high impedances. The attained time resolution was 4.4 ms. In FIGS. 12(a) and (b) the real and negative imaginary parts respectively of the underlying impedance spectrum of one point (122) in the time courses in FIG. 11 is shown. Just five contributing frequencies in the impedance spectrum were sufficient to determine three independent, partially dynamic variables from the impedance spectra. This proves the significantly higher information content of measurements using highly time resolved impedance spectroscopy even in a very limited frequency band in comparison to measuring resistance at only one frequency.

Figure 13:
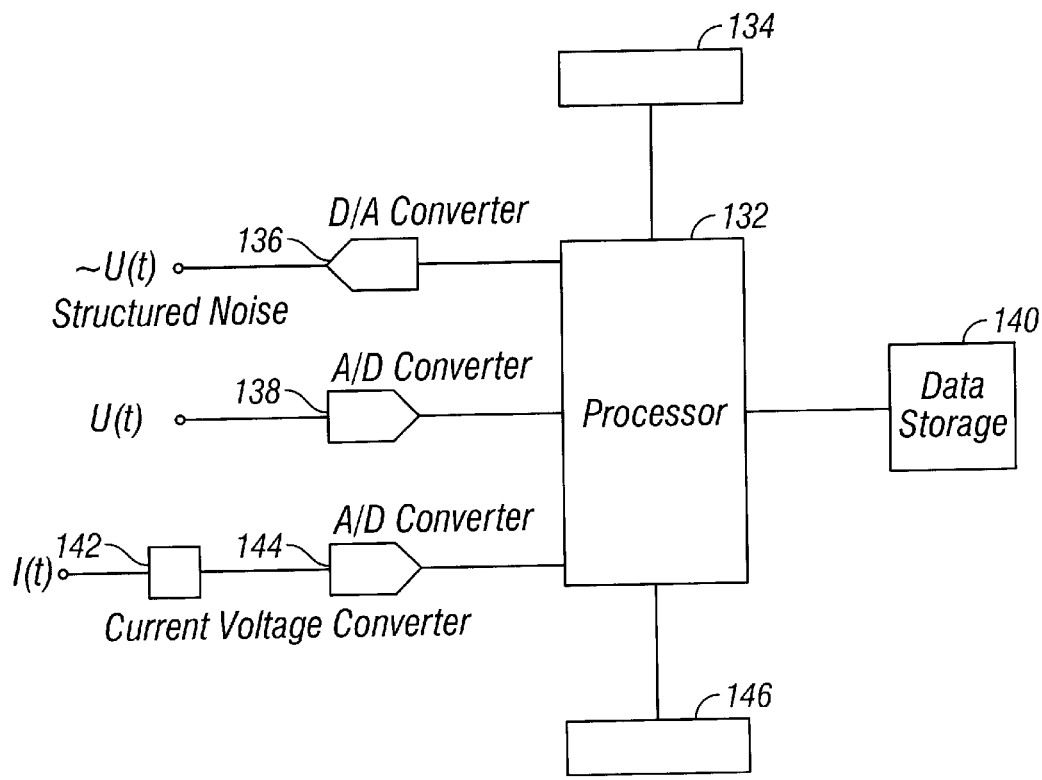
FIG. 13 is a block diagram illustrating one embodiment of the highly time resolved impedance spectroscopy.

FIG. 13 is a block diagram illustrating one embodiment of the highly time resolved impedance spectroscopy. As illustrated in FIG. 13, the basic setup for highly time resolved impedance spectroscopy requires just a few components. A main processor (132) unit controls signal generation and data acquisition on two channels. The data for the structured noise signal are generated by the processor unit according to a stored algorithm, stored in a memory device (134) and the voltage signal is applied to an output after a D to A converter (136). The measured voltage signal U(t) undergoes A to D conversion, at converter (138), at an input channel and is transferred to the memory. At the second input channel, the current signal I(t) is received by a signal conditioner (142) and undergoes current to voltage conversion at an A to D converter (144). The output of the converter (144) is transferred to memory. The measured data of the voltage and current signal are processed and analyzed with a routine stored in a memory device (146), and the results are saved on the data storage media (140). In another embodiment, the two memory devices (134) and (136) are the same memory device.

As described above, the use of the highly time resolved impedance spectroscopy has many advantages over conventional impedance spectroscopy. Some of the advantages include: substantial improvement in the time resolution of impedance spectroscopy; time resolution down to a fraction of each individual frequency in the impedance spectrum; continuous measurement with fast response times; real-time measurements; optimization of the measuring procedure by adapting the perturbation signal and the data processing and analysis to the investigated system; repeated analysis of the measured data records adapted to the focus of the evaluation; highly flexible technique; investigation of dynamic processes that previously could not be measured with impedance spectroscopy such as opening and closing individual ion channels in natural or artificial, free or supported membranes; and highly favorable signal to noise ratio.

The foregoing description details certain embodiments of the invention. It will be appreciated, however, that no matter how detailed the foregoing appears, the invention may be embodied in other specific forms without departing from its spirit or essential characteristics. The described embodiments are to be considered in all aspects only as illustrative and not restrictive and the scope of the invention is, therefore, indicated by the appended claims rather than by the foregoing description. All changes which come within the meaning and range of equivalency of the claims are to be embraced within their scope.

We claim:

1. A method of highly time resolved impedance spectroscopy comprising:
   generating an a.c. voltage perturbation signal and applying it to a system;
   recording the a.c. voltage perturbation signal and a current signal produced in response to the perturbation signal; and
   processing the recorded signals using a non-stationary time to frequency transformation.

2. A method as defined in claim 1, wherein the non-stationary time to frequency transformation is a short time Fourier transform.

3. A method as defined in claim 1, wherein the non-stationary time to frequency transformation is a wavelet transformation.

4. A method as defined in claim 1, wherein the non-stationary time to frequency transformation is a Wigner distribution.

5. A method as defined in claim 1, wherein the recording of the a.c. perturbation signal is continuous.

6. A method as defined in claim 1, wherein the recording of the a.c. perturbation signal is partly continuously recorded.

7. A method as defined in claim 1, wherein the a.c. perturbation signal is structured noise.

8. A method as defined in claim 1, further comprising using a high-performance signal amplifier.

9. A method as defined in claim 1, further comprising a analog-digital conversion of the measuring signals.

10. A method as defined in claim 1, further comprising data processing hardware and software for real-time analysis of the impedance spectra.

11. A method as defined in claim 1, further comprising detection of the conductivity of natural or artificial freely-suspended or substrate-supported lipid membranes with and without ion channels.

12. A method as defined in claim 1, further comprising the use of a frequency range of about 100 Hz to 100 kHz and the logarithmic analysis of the real and imaginary part of the impedance.

13. A method as defined in claim 1, further comprising detection of compounds in solutions with a conductivity changing effect in regard to biomembranes.

14. A method as defined in claim 1, further comprising using a measuring chambers with temperature control and liquid handling.

15. A method as defined in claim 1, further comprising use of a complex nonlinear least square method to fit parameters of an equivalent circuit to the measured impedance spectra.

16. A method as defined in claim 1, further comprising the use of automatic liquid handling systems.

17. A method as defined in claim 1, further comprising the use of multielectrode arrangements.

18. A method as defined in claim 17, further comprising the use of multiple measuring chamber systems with parallel data acquisition and analysis.

19. A method as defined in claim 17, further comprising the use of multiple measuring chamber systems with sequential data acquisition and analysis.

20. A method as defined in claim 1 further comprising the integration in automated production and process flow.

21. An apparatus for measuring impedance spectra with high time resolution, the apparatus comprising:
   a memory device configured to store an algorithm for generation of a voltage perturbation signal and instructions to process and evaluate measured data;
   at least one analog to digital converter configured to receive a signal representing the voltage perturbation signal and to output a digital value representing the perturbation signal, and to receive an electrical current signal representing a system response to the perturbation signal and to output a digital value representing the system response; and
   a processor configured to receive the digital values output by the at least one analog to digital converters, and to receive the algorithm and instructions to process and evaluate measured data from the memory device, and to output a perturbation signal and an impedance spectra, wherein the instructions to process and evaluate measured data comprise a non-stationary time to frequency transformation.

22. The apparatus as defined in claim 21, wherein the non-stationary time to frequency transformation is a short time Fourier transform.

23. The apparatus as defined in claim 21, wherein the non-stationary time to frequency transformation is a wavelet transform.

24. The apparatus as defined in claim 21, wherein the non-stationary time to frequency transformation is a Wigner distribution.

25. The apparatus as defined in claim 21, wherein the perturbation signal is continuously recorded.

26. The apparatus as defined in claim 21, wherein the perturbation signal is partly continuously recorded.

27. The apparatus as defined in claim 21, wherein the perturbation signal is structured noise.

28. The apparatus as defined in claim 21, further comprising use of a complex nonlinear least square method to fit parameters of an equivalent circuit to the impedance spectra.

29. The apparatus as defined in claim 21, further comprising the use of multielectrode arrangements.

30. The apparatus as defined in claim 21, further comprising use of automatic liquid handling systems.

31. The apparatus as defined in claim 21, further comprising use of a multiple measuring chamber systems with parallel data acquisition and analysis.

32. The apparatus as defined in claim 21, further comprising use of a multiple measuring chamber systems with sequential data acquisition and analysis.

33. The apparatus as defined in claim 21, further comprising a measuring cell or chamber for detection of the conductivity of natural or artificial freely-suspended or substrate-suspended lipid membranes with or without ion channels.

34. The apparatus as defined in claim 21, further comprising a measuring cell or chamber for detection of compounds in solutions with a conductivity changing effect in regard to biomembranes.

35. The apparatus as defined in claim 21, further comprising the use of a measuring cell or chamber with temperature control and liquid handling.

* * * * *

UNITED STATES PATENT AND TRADEMARK OFFICE
CERTIFICATE OF CORRECTION

PATENT NO. : 6,556,001 B1
DATED : April 29, 2003
INVENTOR(S) : Wiegand et al.

It is certified that error appears in the above-identified patent and that said Letters Patent is hereby corrected as shown below:

Title page,
Insert Item -- [30] Foreign Application Priority Data
October 12, 1999 (DE) 19949107.0
April 15, 2000 (DE) 10018745.5 --
Item [76], Inventors, the addresses should read as follows:
-- Gerald Wiegand, 1194 Guerrero St., San Francisco, CA (US)
Erich Sackman, Am Hochacker 47, D-81827, Muenchen (GERMANY) --

Column 3,
Line 63, "time $\iota$" should read as -- time $\tau$ --;

Column 7
Line 1, in Equation 3 both instances of "$\iota$" should read as -- $\tau$ --;
Line 1, the portion of Equation 3 that reads as "$e^{-1\omega t}$" should read as -- $e^{-i\omega t}$ --;
Lines 4 through 66, all instances of "$\iota$" should read as -- $\tau$ -- ;
Lines 57 through 61, the portion of Equation 5 that reads as "$e^{i\omega n T_a}$" should read as -- $e^{-i\omega n T_a}$ --;

Column 8,
Line 38, the portion of Equation 9 that reads as "$e^{-1\omega_0 t}$" should read -- $e^{-i\omega_0 t}$ --;
Line 53, "$\Delta\iota$" should read as -- $\Delta\tau$ --;

Column 9,
Line 30, "$\Delta\iota$" should read as -- $\Delta\tau$ --;
Line 43, please delete the period between "processes" and "in"
Lines 48 through 49, the portion of Equation 10 that reads as "IM" should read as -- Im --;
Lines 48 through 49, the portion of Equation 10 that reads as "$e^{1\varphi(\omega)}$" should read as -- $e^{i\varphi(\omega)}$ --;
Line 62, "$\Delta\iota$" should read as -- $\Delta\tau$ --;

UNITED STATES PATENT AND TRADEMARK OFFICE
CERTIFICATE OF CORRECTION

PATENT NO. : 6,556,001 B1
DATED : April 29, 2003
INVENTOR(S) : Wiegand et al.

It is certified that error appears in the above-identified patent and that said Letters Patent is hereby corrected as shown below:

Column 12,
Line 13, both instances of "ι" should read as -- τ --.

Signed and Sealed this

Twenty-fifth Day of January, 2005

JON W. DUDAS
*Director of the United States Patent and Trademark Office*